United States Patent
Williams et al.

(10) Patent No.: US 8,038,623 B2
(45) Date of Patent: Oct. 18, 2011

(54) CALIBRATION OF IN VIVO BLOOD PRESSURE SENSORS

(75) Inventors: Jonathan Williams, Montville, NJ (US);
Shrenik Daftary, New York, NY (US);
Boris Leschinsky, Mahwah, NJ (US)

(73) Assignee: Datascope Investment Corp., Mahwah, NJ (US)

( * ) Notice: Subject to any disclaimer, the term of this patent is extended or adjusted under 35 U.S.C. 154(b) by 0 days.

(21) Appl. No.: 12/661,840

(22) Filed: Mar. 25, 2010

(65) Prior Publication Data

US 2010/0191129 A1     Jul. 29, 2010

Related U.S. Application Data

(63) Continuation of application No. 11/975,055, filed on Oct. 17, 2007, now Pat. No. 7,722,544.

(51) Int. Cl.
*A61B 5/02* (2006.01)
(52) U.S. Cl. ............... 600/486; 600/485; 600/500
(58) Field of Classification Search ............. 600/485, 600/486, 500, 504, 505, 435
See application file for complete search history.

(56) References Cited

U.S. PATENT DOCUMENTS

| | | | |
|---|---|---|---|
| 4,223,682 A | 9/1980 | Sherman |
| 5,158,529 A | 10/1992 | Kanai |
| 5,384,028 A | 1/1995 | Ito |
| 5,913,814 A | 6/1999 | Zantos |
| 6,120,457 A | 9/2000 | Coombes et al. |
| 6,245,008 B1 | 6/2001 | Leschinsky et al. |
| 2004/0097813 A1 | 5/2004 | Williams |
| 2005/0228301 A1 | 10/2005 | Banet et al. |
| 2006/0287569 A1 | 12/2006 | Schock et al. |
| 2007/0027393 A1 | 2/2007 | Williams et al. |

OTHER PUBLICATIONS

International Search Report, PCT/US2008/11853.

*Primary Examiner* — Patricia Mallari
*Assistant Examiner* — Michael D'Angelo
(74) *Attorney, Agent, or Firm* — Jarrett L. Silver

(57) ABSTRACT

A method for performing an in-vivo calibration of a blood pressure sensor that is associated with an in-vivo balloon system. The method involves monitoring a patient's blood pressure by observing the system gas pressure while at the same time monitoring the patient's blood pressure through the sensor. The blood pressure measurements obtained by monitoring the system gas pressure are used as reference, or "true," blood pressure measurements, and an "offset" is determined between the reference blood pressure measurements and the blood pressure measurements obtained through the sensor. The offset can be stored in a memory, which may also store sensor sensitivity data. The offset and/or sensitivity data may be used to adjust future measurements obtained from the sensor, thereby generating calibrated sensor measurements.

20 Claims, 12 Drawing Sheets

CALIBRATION OF IN VIVO BLOOD PRESSURE SENSORS

CROSS-REFERENCE TO RELATED APPLICATION

The present application is a continuation of U.S. patent application Ser. No. 11/975,055, filed Oct. 17, 2007 which is related to commonly-owned co-pending U.S. patent application Ser. No. 11/494,973, filed Jul. 27, 2006, the disclosures of which are hereby incorporated by reference herein.

FIELD OF THE INVENTION

The present invention relates generally to calibrating in-vivo type blood pressure sensors while such sensors are in-vivo. More particularly, the present invention relates to in-vivo calibration of blood pressure sensors that are associated with a balloon, or balloon-like construct, that is intended for in-vivo use. Still more particularly, the present invention relates to in-vivo calibration of blood pressure sensors that are associated with an in-vivo balloon, or balloon-like construct, by using electronically-stored correction data.

BACKGROUND OF THE INVENTION

In the practice of medicine there are many instances in which accurate measurement of patient blood pressure is required. In some instances, it is necessary to obtain accurate blood pressure measurements from particular locations within a patient's body, or "in-vivo." Among those instances in which it is necessary to obtain accurate in-vivo blood pressure measurements are procedures involving the use of an in-vivo balloon or in-vivo balloon-like construct. (In the interest of brevity the term "balloon" will be used throughout this description to denote both balloons and balloon-like constructs.)

SUMMARY OF THE INVENTION

The present invention provides a method for performing an in-vivo calibration of a blood pressure sensor that is associated with an in-vivo-balloon system, the sensor and balloon being associated such that the sensor is in-vivo when the balloon is in-vivo. The method involves controlling the inflation state of the balloon so that a gas pressure in the system is indicative of a patient's blood pressure, monitoring the patient's blood pressure by observing the shuttle gas pressure while at the same time monitoring the patient's blood pressure through the sensor, and using blood pressure measurements obtained by monitoring the shuttle gas pressure as reference, or "true," blood pressure measurements to determine an "offset" between blood pressure measurements obtained through the sensor and the reference blood pressure measurements. After determining an offset between the blood pressure measurements obtained through the sensor and the reference, or "true," blood pressure measurements, the offset can be used to adjust future measurements obtained from the sensor to thereby generate calibrated sensor measurements.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

One type of procedure that uses an in-vivo balloon is intra-aortic balloon (IAB) therapy. By way of illustration, further description will be provided in the context of IAB therapy.

Intra-aortic balloon therapy is frequently prescribed for patients who have suffered a heart attack or some other form of heart failure. In such therapy, a thin balloon is inserted through an artery into the patient's aorta. The balloon is connected through a series of tubes to a complex drive apparatus which causes the balloon to inflate and deflate repeatedly in time with the patient's heartbeat, thereby removing some of the load from the heart and increasing blood supply to the heart muscle during the therapy period.

Figure 1:
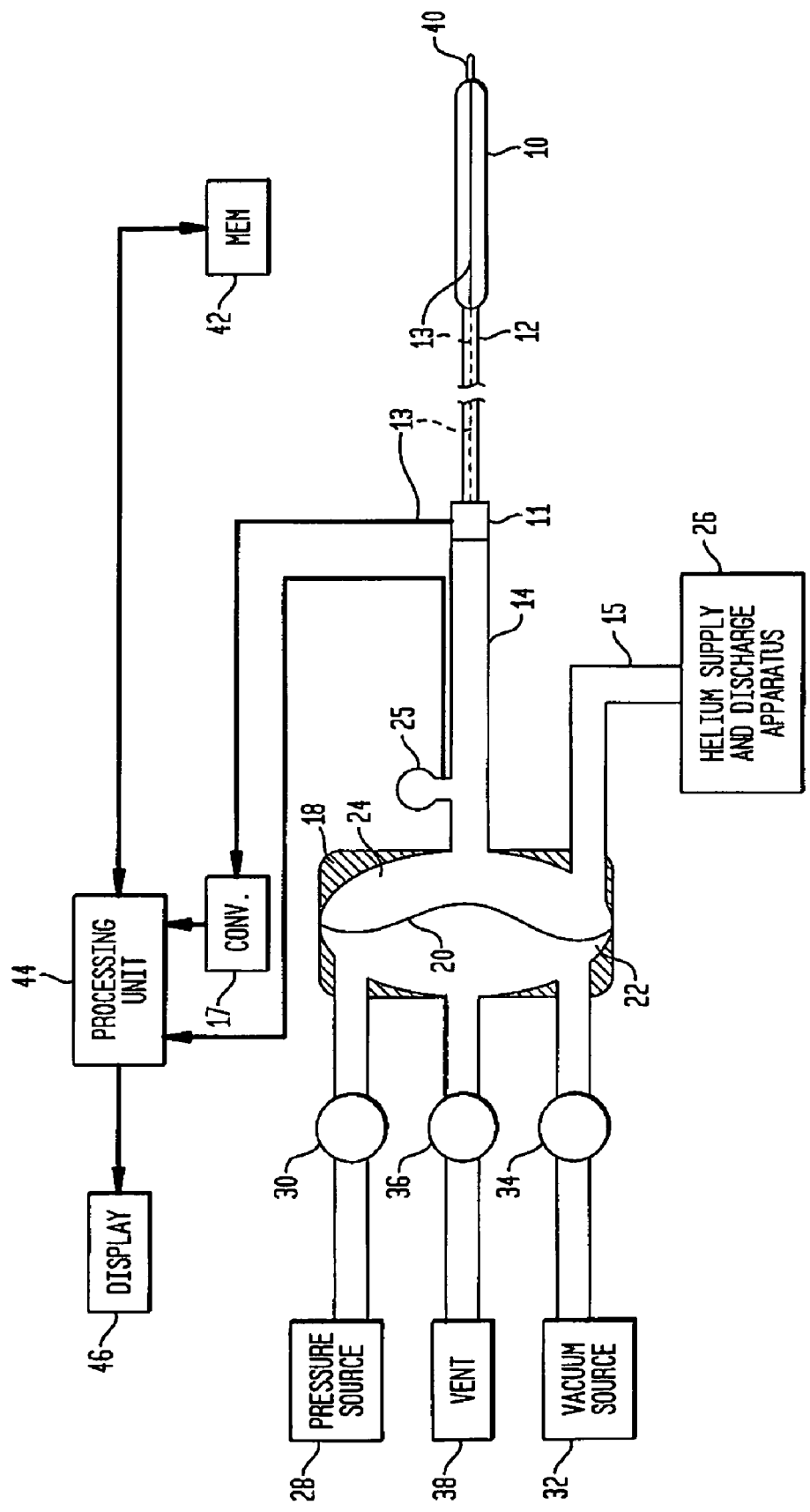
FIG. 1 is a schematic view of an intra-aortic balloon system in which measurements of shuttle gas pressure are used to calibrate an in-vivo fiber optic blood pressure sensor.

The inflation/deflation apparatus supplies positive pressure for expanding the balloon during an inflation cycle and negative pressure for contracting the balloon during a deflation cycle. An IAB apparatus is shown schematically in FIG. 1. In the FIG. 1 apparatus, an intra-aortic balloon (IAB) 10 is surgically inserted into a patient's aorta and is connected through a catheter 12 having a small diameter lumen, a connector 11, and an extender 14 having a relatively large diameter lumen to a pneumatic isolator 18 divided by a pliant membrane 20 into a primary side 22 and a secondary side 24. Accordingly, all elements to the left of membrane 20 in FIG. 1 are referred to as being on the "primary side" of the apparatus, and all elements to the right of membrane 20 in FIG. 1 are referred to as being on the "secondary side" of the apparatus.

The entire volume between membrane 20 and balloon 10 is completely filled with a gas, such as helium, supplied by a gas source, such as helium supply and discharge apparatus 26.

The gas source is coupled to the secondary side of the isolator via a fill/purge line 15. A gas pressure sensor 25 is provided for monitoring the gas pressure within the secondary side of the IAB apparatus. For purposes of discussion, the gas present within the secondary side of the IAB system is referred to as the "shuttle gas." Accordingly, pressure sensor 25 is the "shuttle gas pressure sensor" and it measures "shuttle gas pressure."

A positive pressure source 28 is connected through a solenoid valve 30 to the input or primary side 22 of isolator 18. Similarly, a negative pressure source 32 is connected through a solenoid valve 34 to the input or primary side 22 of isolator 18. The primary side 22 of isolator 18 is also connected through a solenoid valve 36 to a vent or exhaust port 38. In such systems, the isolator, gas source, negative and positive pressure sources, vent port and their associated valves together comprise a reusable drive unit, and the extender, catheter and balloon are disposable so as to accommodate sterility concerns.

During an inflation cycle, solenoid valve 30 is opened to permit positive pressure from positive pressure source 28 to enter primary side 22 of isolator 18. This positive pressure causes membrane 20 to move toward secondary side 24, thereby forcing the shuttle gas in the secondary side to travel toward and inflate balloon 10. For deflation, solenoid valve 30 is closed and solenoid valve 36 is opened briefly to vent the gas from primary side 22 to atmosphere, after which valve 36 is closed. Solenoid valve 34 is then opened, whereupon negative pressure source 32 creates a negative pressure on the primary side 22 of isolator 18. This negative pressure pulls membrane 20 toward primary side 22, whereby the shuttle gas is drawn out from the balloon.

Maximum patient benefit is achieved when the timing of IAB inflation and deflation is correct. To meet this requirement, the patient's blood pressure waveform must be accurately monitored. The monitored signal is then analyzed for key cardiac events.

Accordingly, the IAB system as shown in FIG. 1 includes a pressure sensor 40 proximal to the front end of the balloon for the purpose of monitoring a patient's blood pressure during IAB therapy. Sensor 40 can be a fiber optic sensor that measures pressure by observing how light is reflected from a diaphragm which moves in response to pressure changes. The optical signal generated by sensor 40 is passed back to a monitor outside of the patient's body via a fiber optic line 13 that passes through the balloon 10, catheter 12 and connector 11 (connector 11 being a pneumatic and fiber optic connector suitable for accommodating both a fiber connection and a pneumatic connection between the catheter and extender). The optical "pressure" signal transmitted through line 13 is converted into an electrical signal by converter module 17, and the result is an electrical signal that is indicative of the patient's blood pressure as sensed through sensor 40.

It has been recognized that in order to obtain accurate blood pressure measurements from in-vivo blood pressure sensors it is necessary to calibrate such sensors individually and repeatedly. One reason calibration is necessary is that the sensors are subject to inconsistencies in their manufacture which cause their performance to vary from sensor-to-sensor. Another reason is that the performance of a sensor varies over time as the sensor is subjected to environmental stress. Thus, even if a sensor is calibrated prior to leaving the factory, it requires recalibration from time-to-time to account for such environmental stress.

In prior systems, the calibration process is initiated by a clinician who adjusts the "zero point" of the sensor by exposing the sensor to atmospheric pressure before it is placed in the patient and applying a correcting offset to compensate for any amount that the sensor reading deviates from atmospheric pressure. For example, if the sensor reads 10 mmHg gauge pressure when exposed to atmospheric pressure (i.e. the sensor has a 10 mmHg offset), then a 10 mmHg correcting offset is applied to "zero" the sensor. That is, 10 mmHg is subtracted from all future sensor readings. This type of calibration has several drawbacks. One drawback is that after the sensor is inserted into the patient, re-zeroing is not practical, since re-zeroing requires the removal of an already placed sensor. Another drawback is that the application of a fixed compensating-offset does not account for "drift" (or "variability or errors") in the sensor's scale factor (also called "sensitivity", "gain", or "slope"). More specifically, the sensor error may be different at pressures other than atmospheric so that the offset necessary to achieve an accurate reading when the sensor is exposed to atmospheric pressure may not yield an accurate reading when the sensor is exposed to a different pressure.

Further, the prior systems did not account for the variation-over-time of the sensor's offset and sensitivity. Thus, even if the system was correctly calibrated in given instance, the system could be thrown out of calibration due to offset and/or sensitivity deviations occurring over the course of time.

In view of the drawbacks associated with prior in-vivo sensor systems, the present inventors have recognized a need for a calibration scheme which accounts for both sensor offset and sensor sensitivity, and which accounts for time-variation of such offset and sensitivity. However, the inventors have further recognized that sensor manufacturing technology has improved such that in-vivo blood pressure sensors can be manufactured with sensitivity characteristics that are stable over time.

Accordingly, the inventors have provided a system and method for calibrating an in-vivo blood pressure sensor in which the sensor sensitivity characteristic is determined once and the sensor offset is determined as frequently as necessary. When the sensor is in use, calibrated (or "corrected") blood pressure readings are obtained by applying a sensitivity adjustment and an offset adjustment to uncalibrated or ("raw") blood pressure readings. In one embodiment, the sensor's sensitivity characteristic is determined at the time of sensor manufacture and the sensor's offset is determined in-vivo during, for example, an IAB therapy session. In such embodiment, use of the sensor does not include determination of the sensor's sensitivity, but may include determination of the sensor's offset.

The present embodiments relate to calibrating in-vivo blood pressure sensors that are associated with an in-vivo balloon by using measurements of gas pressure within the balloon. For purposes of clarity of presentation, the detailed description of the embodiments will focus on the IAB therapy implementation. In view of such detailed description, one skilled in the art can readily apply the embodiments in other in-vivo contexts.

More particularly, the detailed description will focus on implementation in the IAB system similar shown in FIG. 1. In view of the detailed description, one skilled in the art will be able to readily apply the embodiments in IAB systems other than that depicted in FIG. 1. For example, after reading the detailed description, one skilled in the art will be able to apply the embodiments to an IAB system that uses a bellows in lieu of some or all of the drive unit elements depicted in FIG. 1.

In a preferred embodiment, calibration of a fiber optic sensor proximal an intra-aortic balloon is performed in-vivo. Of course, while the calibration of a fiber optic sensor is described in detail, the embodiment may be applied to any type of in-vivo sensor, including any type of electronic sensor and any type of opto-electronic sensor.

Referring now to FIG. 1, there is shown a schematic view of an intra-aortic balloon system in accordance with an embodiment. In the FIG. 1 system, correction data for the fiber optic blood pressure sensor 40 is stored in a memory 42. The correction data is applied to "raw" fiber optic sensor measurements by a processing unit 44 and may include data used to compensate for the sensor sensitivity characteristic and the sensor offset. The data used to compensate for the sensor sensitivity characteristic may be determined at the time of sensor manufacture and provided with the sensor. The data used to compensate for the sensor offset may be updated while the sensor is in-vivo.

In one embodiment, the memory is incorporated into the connector 11. In another embodiment, the memory is incorporated into the processing unit. In any event, suitable types of memory that may serve as memory 42 include, but are not limited to, integrated circuit random access memory (RAM), integrated circuit read only memory (ROM), optical disk storage media, and magnetic disk storage media.

The correction data may be stored as a series of values corresponding to respective sensor readings. For example, if the sensor reads 10 mmHg (gauge pressure) when exposed to atmospheric pressure, reads 10.5 mmHg when exposed to 1 mmHg, and reads 11 mmHg when exposed to 2 mmHg, then the respective correction values are −10 mmHg, −9.5 mmHg, and −9 mmHg.

Figure 2A:
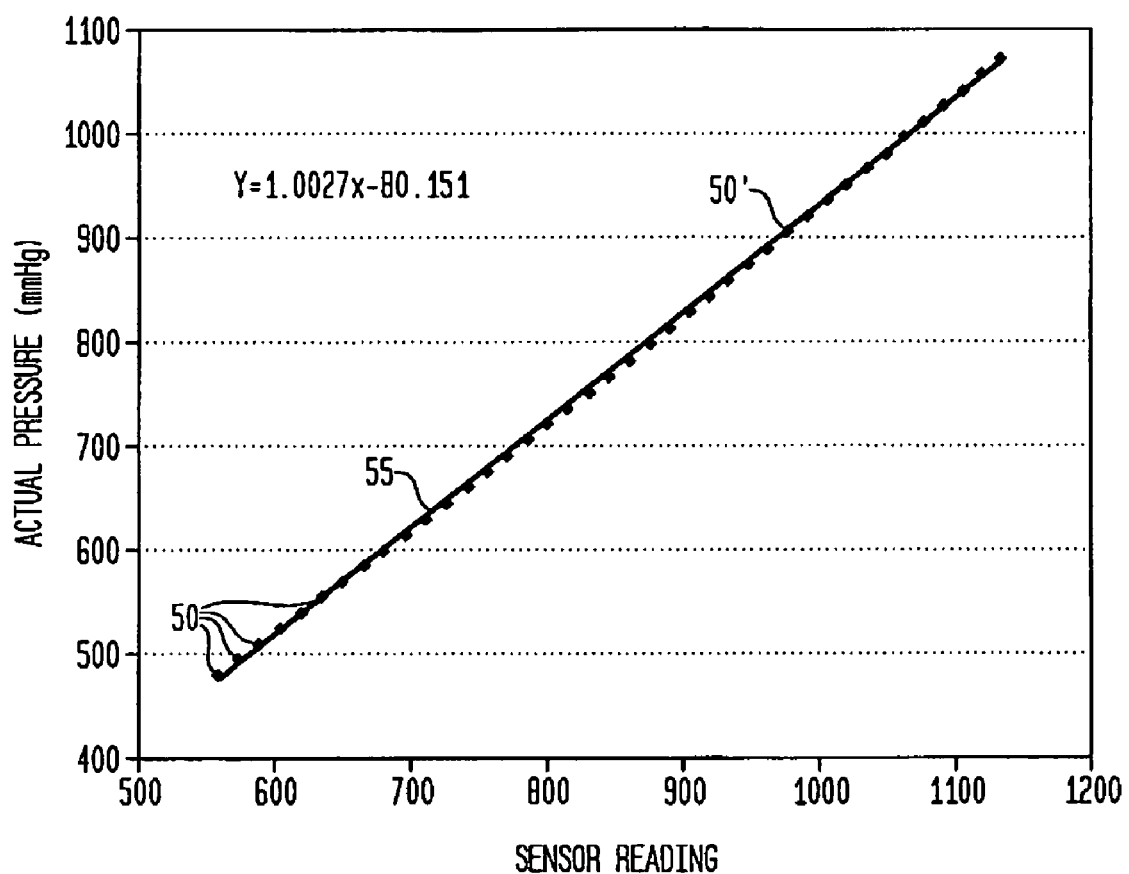
FIGS. 2A and 2B are graphs useful in describing how sensor "sensitivity" and sensor "offset" information is stored according to an embodiment.
Figure 2B:
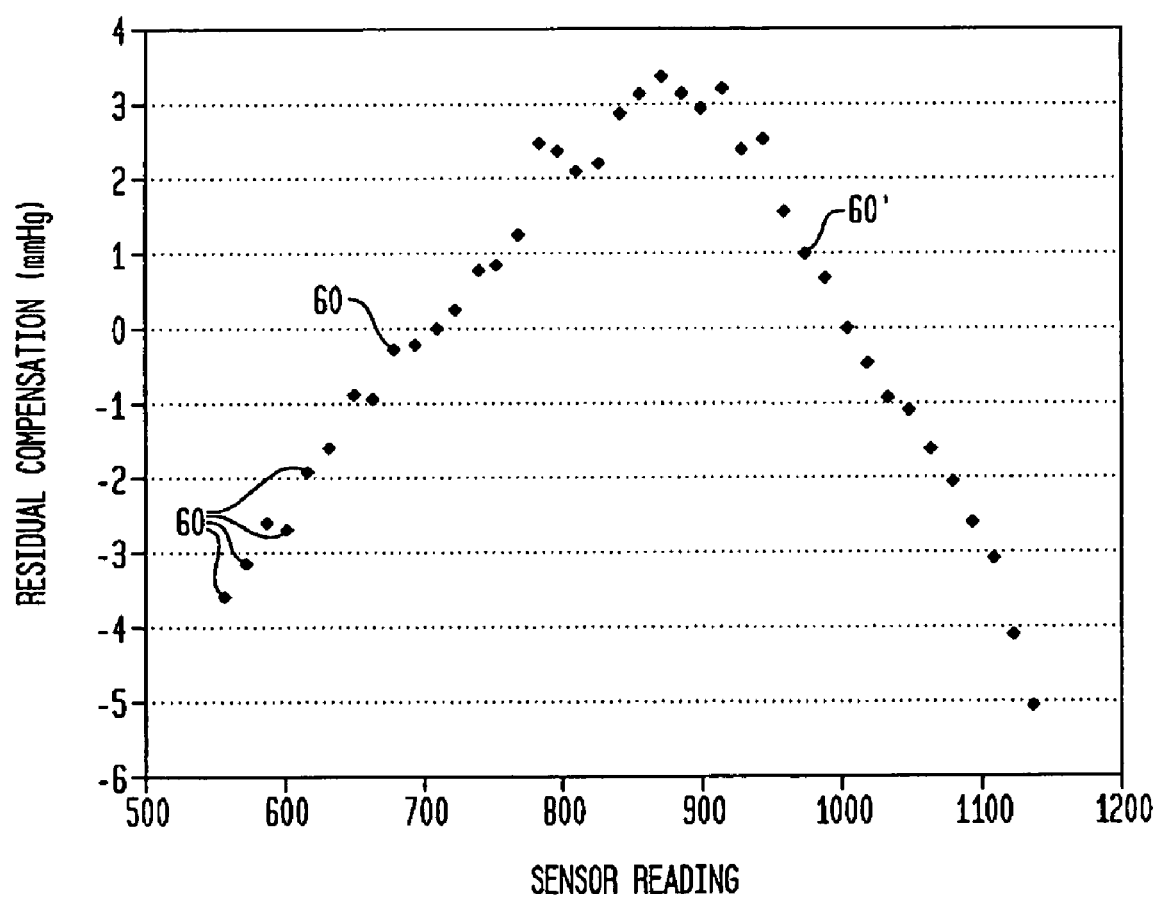

In one embodiment, the correction data is stored as a combination of an equation and a series of residual values. FIGS. 2A and 2B are graphs useful in describing how correction data is stored according to an embodiment. FIG. 2A is a graph in which the x-axis (abscissa) represents blood pressure as measured through a blood pressure sensor, and the y-axis (ordinate) represents actual blood pressure. The graph includes a multiple of points 50. Each of points 50 links a blood pressure sensor reading to an actual blood pressure. Thus, for example point 50' shows that a sensor reading of about 977 mmHg (absolute) corresponds to an actual blood pressure reading of about 900 mmHg (absolute). A line 55 depicts a linear approximation of the relationship defined by points 50, namely the relationship between the sensor readings and the respective actual blood pressures. The equation describing the line provides a mathematical formula for approximating actual blood pressures based on sensor readings. In FIG. 2A, the line is described by the equation: $y=1.0027x-80.151$.

In an embodiment, the approximations generated through use of the equation are refined such that actual blood pressures, or substantially actual blood pressures, (i.e. "calibrated" blood pressures) are generated on the basis of the sensor readings. FIG. 2B is a graph in which the x-axis (abscissa) represents blood pressure as measured through a blood pressure sensor, and the y-axis (ordinate) represents "residual compensation". The residual compensation refers to an adjustment that is applied to the linear approximation such that calibrated blood pressures can be obtained from sensor readings. The graph includes a multiple of points 60. Each of points 60 links a blood pressure reading to a residual compensation. For example point 60' shows that a sensor reading of 975 mmHg (absolute) corresponds to a residual compensation of 1 mmHg.

Thus, when a sensor reading of "x" is observed the value "x" is used in the linear approximation equation to yield a linear approximation, "y", of the actual blood pressure. Then, the appropriate residual compensation is applied to the approximation "y" to yield the calibrated blood pressure. That is, the equation of FIG. 2A ($y=1.0027x-80.151$) is applied to a sensor reading of "x" to yield an approximation "y", the residual compensation for "x" is determined from the FIG. 2B data, and the residual compensation is applied to "y" to yield the calibrated blood pressure associated with the sensor reading of "x". The slope of the equation (1.0027) corresponds to the sensitivity characteristic of the sensor, and the offset of the equation (−80.151) corresponds to the sensor offset. In an embodiment, the offset of the equation is re-calculated (i.e. the system is "calibrated") on an as-needed basis to correct for variations in the sensor offset that occur with the passage of time.

It should be understood that the embodiments are not limited to linear approximations for approximating actual blood pressures based on sensor readings. Upon viewing this disclosure, one skilled in the art will readily appreciate the wide range of mathematical relationships that may be used to approximate actual blood pressures based on sensor readings. For instance, a polynomial fit may be performed on the data of FIG. 2A in order to derive a polynomial equation relating the actual blood pressures, or approximate actual blood pressures, to sensor readings.

It should be further understood that interpolation may be employed to determine residual compensation values corresponding to sensor measurements that fall between data points. For example, in FIG. 2B there is no data point corresponding to a sensor reading of 1000 mmHg; however, a residual compensation value for a sensor reading of 1000 mmHg may be generated by interpolating between the data points bounding 1000 mmHg.

In one embodiment the system is calibrated at the initiation of intra-aortic balloon ("IAB") therapy and thereafter as-needed. Factors considered in determining when to calibrate may include elapsed time from the most recent calibration, patient conditions (e.g. the patient's systolic and diastolic pressure, and/or the patient's body temperature), and/or environmental changes.

In one IAB implementation, the system is calibrated by suspending pumping and collecting calibration data. More particularly, pumping is suspended while simultaneous readings of the patient's aortic blood pressure are obtained from two pressure measurement channels. One channel conveys readings from the fiber optic pressure sensor 40 located at the tip of the IAB. The other channel conveys readings from the shuttle gas pressure sensor 25. The data readings from the two channels are collectively referred to as the calibration data.

Normally, during pumping, the shuttle gas pressure sensor measures the pressure of the gas used to inflate and deflate the balloon. However, when conditions are correct, measurements of patient blood pressure can be obtained from this sensor. In one embodiment, obtaining measurements of patient blood pressure through the shuttle gas pressure sensor requires that: (1) pumping is suspended; and (2) the balloon is held in a partially inflated state while data is collected, i.e., the balloon's membrane is flaccid while data is collected. When the balloon is in a partially inflated state, the pressure of the gas within the IAB is identical to the pressure on its exterior, i.e., the pressure of the gas can be used as a "surrogate" for patient blood pressure.

The fidelity of the calibration process is optimized when the IAB is inflated to a "target displacement volume." Typically, this target displacement volume for adult IABs is 10 cc.

After calibration data is collected, the IAB is refilled to its "normal" inflation volume, and pumping resumes. In the background, the collected calibration data is processed by an algorithm that calibrates the fiber optic sensor. Such algorithm may be implemented, for example, by the processing unit 44 of FIG. 1.

The calibration process assumes that the shuttle gas pressure sensor 25 is accurate and uses its measurements as a reference to calibrate the fiber optic sensor 40. Once calibration is complete, patient blood pressure measurements are derived solely from the corrected measurements of the fiber optic sensor and pumping resumes. As an option, the corrected measurements may be displayed by, for example, display 46 of FIG. 1.

Figure 3:
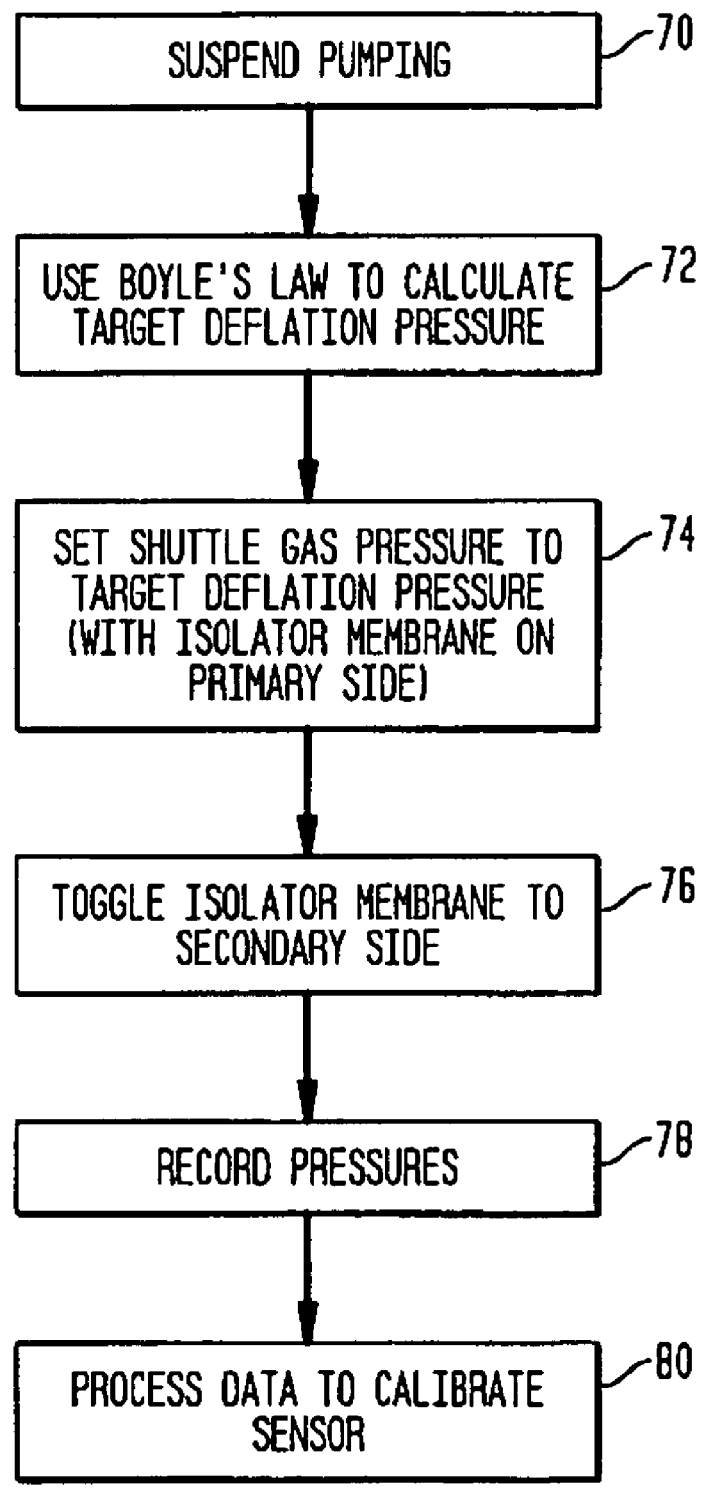
FIG. 3 is a flow chart showing how the IAB system of FIG. 1 is calibrated in accordance with an embodiment.

FIG. 3 is a flow chart showing one way in which the IAB system of FIG. 1 is calibrated in accordance with an embodiment. The calibration process initially involves setting the IAB system such that the balloon can be used to provide reference, or "true," blood pressure readings. The first step in setting up the IAB system to provide balloon-based blood pressure measurements is the suspension of pumping (step 70). Following the suspension of pumping, the IAB is filled to a target displacement volume for calibration. Achieving the correct target displacement volume is critical since the balloon must be kept in a flaccid state throughout the period in which calibration data is collected. If the balloon is allowed to completely inflate or deflate during the time when calibration data is collected, then the blood pressure readings obtained through the shuttle gas pressure sensor 25 will be unusable for calibration.

A procedure for achieving the target displacement volume is discussed in the context of an IAB system in which the volume of gas in the balloon can not be directly measured. Further, it is presumed that the volume of gas present within the secondary side of the IAB system can not be directly measured.

In order to properly adjust the volume of gas in the secondary side of the IAB system such that the target displacement volume is achieved, Boyle's law is relied upon. More specifically, Boyles law ($P1*V1=P2*V2$) is used to relate the pressure (P1) and volume (V1) of the shuttle gas under a first condition (deflation) to the pressure (P2) and volume (V2) of the shuttle gas under a second condition (partial inflation). By allowing P2 to denote the shuttle gas pressure when the target displacement volume is achieved, solving Boyle's law for P1 determines the "target deflation pressure," that is, the pressure necessary in the deflation condition to achieve the target displacement volume upon transition to the second condition (step 72).

In practice, the first condition for calculation of target deflation pressure is that of the membrane 20 being on the primary side of the isolator 18 and the balloon 10 being completely deflated. The second condition is that of the membrane being on the secondary side of the isolator and the balloon being filled to its target displacement volume. Given the two conditions and using the term "dead volume" to denote the total volume of gas present in the combination of sensor 25, extender 14, catheter 12 and fill/purge line 15, the target deflation pressure is computed according to the following implementation of Boyle's law: P1=target deflation pressure; V1=isolator volume+dead volume; P2=load pressure; and V2=target displacement volume+dead volume. Using these values in $P1*V1=P2*V2$ and solving for target deflation pressure yields: target deflation pressure=(load pressure*(target displacement volume+dead volume))/(isolator volume+dead volume), wherein the "load pressure" is the expected pressure that will impinge upon the balloon when it is inflated (i.e. the expected nominal value of patient blood pressure). It is noted that use of Boyle's law in this manner assumes that the target displacement volume, isolator volume, and dead volume have been determined. A target displacement volume of 10 cc and an isolator volume of 73.5 cc have been used in an illustrative system.

A technique for determining the dead volume is disclosed in commonly-owned co-pending U.S. patent application Ser. No. 11/494,973, filed Jul. 27, 2006, the disclosure of which is incorporated by reference herein. For sake of brevity of presentation, the description of the technique disclosed in the '973 application will not be repeated in the present description. However, it is noted that such technique is applicable in the current context.

As an alternative to calculating the dead volume in accordance with the technique discussed in the '973 application, an indication of the dead volume may be stored in memory 42. In this manner, the value of the dead volume can be readily determined by reading from the memory. In one example, the volume of balloon 10 is stored in memory 42 and processing unit 44 may read the balloon volume from the memory and infer the dead volume from the balloon volume. In another example, the dead volume may be calculated in accordance with the technique discussed in the '973 application and then stored in the memory for recall upon demand, thereby requiring that the '973 technique be performed only once per system, with the result being available for any subsequent calculations for which the dead volume is required.

Figure 4:
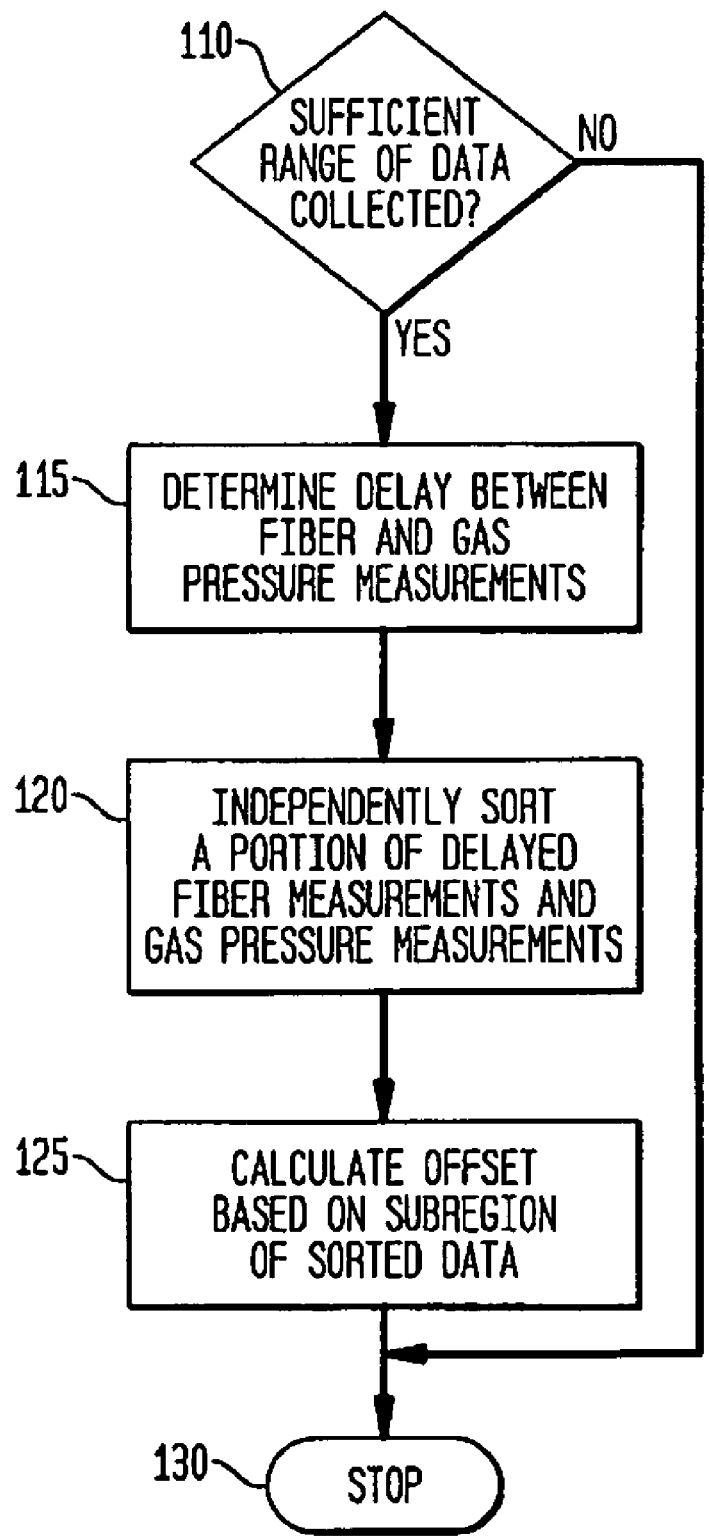
FIG. 4 is a flow chart showing how blood pressure measurements obtained via an IAB system balloon and blood pressure measurements obtained via a fiber optic sensor associated with the balloon are processed to determine an offset between the two types of measurements.

The dead volume is used along with Boyle's law to calculate the "target deflation pressure" (step 72 of FIG. 4). The target deflation pressure is the shuttle gas pressure that must exist when the balloon is deflated and the membrane is against the primary side of the isolator, such that toggling the membrane to the secondary side of the isolator will fill the balloon to the target displacement volume. Once, the dead volume is calculated, the target deflation pressure is computed according to the following implementation of Boyle's law: P1=target deflation pressure; V1=isolator volume+dead volume; P2=load pressure; and V2=target displacement volume+dead volume. Using these values in $P1*V1=P2*V2$ and solving for target deflation pressure yields: target deflation pressure=(load pressure*(target displacement volume+dead volume))/(isolator volume+dead volume).

It should be noted that the dead volume needs to be determined only once for the given combination of sensor 25, extender 14, catheter 12 and fill/purge line 15 since the dead volume is a system constant. Thus, the dead volume does not need to be determined each time the sensor is calibrated.

Once the target deflation pressure has been calculated, shuttle gas is added and/or removed from the secondary side of the system, as the membrane remains on the primary side, until the shuttle gas pressure equals the target deflation pressure (step 74). The shuttle gas is added and/or removed from the secondary side via the fill/purge line 15 and helium supply and discharge apparatus 26. Once the target deflation pressure has been achieved, the membrane is fully toggled to partially inflate the balloon (step 76). Upon toggling of the membrane, the balloon is ready to be used to measure blood pressure. Once the system has been set up to measure blood pressure via the balloon, balloon-based blood pressure measurements and fiber optic blood pressure measurements are recorded for a period of time (step 78). The recorded measurements are then processed to calibrate the fiber optic sensor (step 80).

Before discussing how the recorded measurements are processed, it is important to note the differences between the "shuttle gas pressure channel," through which the balloon-based blood pressure measurements are obtained, and the "fiber optic channel," through which the fiber optic blood pressure measurements are obtained. The frequency response of the shuttle gas channel differs significantly from that of the fiber optic channel. The fiber optic pressure sensor is in direct contact with the patient blood and directly measures patient blood pressure. The pressure signal is transmitted optically and processed by low delay, high bandwidth circuitry. For this reason, it has high bandwidth, low time delay and good fidelity. The shuttle gas channel measures patient blood pressure indirectly via a pneumatic transmission pathway. The pneumatic transmission process delays the pressure signal and suppresses its higher frequencies. The effects of the transmission process should be taken into account when comparing data from the gas channel and optical channel.

Referring now to FIG. 4, there is shown a flow chart depicting how blood pressure measurements obtained via an IAB system balloon and blood pressure measurements obtained from a fiber optic sensor associated with the balloon are processed to determine an offset between the two types of measurements. The steps depicted in FIG. 4 will be described briefly with references to FIG. 4, and then in more detail with references to FIGS. 5-7.

It should be noted that in the process of FIG. 4, the fiber optic measurements that are used to compute an offset may be "raw" fiber optic measurements. That is, they may be measurements obtained through the fiber optic sensor with no applied correction. Alternatively, the fiber optic measurements that are used to compute the offset may be corrected measurements, in which case the offset computed in FIG. 4 may be an offset that is relative to a previously stored offset. For example, if the fiber optic measurements that are used in FIG. 4 are measurements corrected according to the data of FIGS. 2A and 2B, then the offset computed in FIG. 4 will be an offset relative to −80.151 (the offset associated with the equation describing line 55).

For purposes of brevity of description, FIGS. 4-7 will be described in the context of using "raw" fiber optic measurements to compute an offset. Upon review of such description, those skilled in the art will readily appreciate how the embodiments may be implemented in the context of using corrected fiber optic measurements to compute an offset.

Referring now to FIG. 4, the first step in determining an offset is verifying that a sufficient range of data has been collected (step 110). In one embodiment, a sufficient range of data is collected when both the gas pressure measurements and fiber measurements exhibit a range that is greater than 4 mmHg. In another embodiment, a sufficient range of data is collected when both the gas pressure measurements and fiber measurements exhibit a range that is greater than 10 mmHg. In still another embodiment, a sufficient range of data is collected when both the gas pressure measurements and fiber measurements fall within a "physiological range" (e.g. between 10 mmHg and 210 mmHg, gauge pressure). However it should be noted that the embodiments are not limited to these illustrative ranges.

If a sufficient range of data has not been collected, calibration is not performed and processing stops (step 130). If a sufficient range of data has been collected, processing continues (steps 115-125).

Upon the collection of a sufficient range of data, the delay between the fiber and gas pressure measurements is determined (step 115). Next, a portion of the fiber measurements, as shifted according to the delay computed in step 115, is sorted along with a corresponding portion of the gas pressure measurements (step 120). It is important to note that the term "sorting" refers to listing measurements in order of their value, from lowest to highest; although an option is to list the measurements from highest to lowest. Finally, an average is calculated for the difference between the fiber measurements and gas pressure measurements within a sub-region of the sorted measurements (step 125). The calculated average represents the sensor offset. Such offset may be subtracted from subsequent fiber measurements to provide corrected (or "calibrated") fiber measurements.

Having provided an overview of the steps involved in the process of generating an offset between fiber optic sensor measurements and balloon-based measurements, the process will now be described in detail with references to FIGS. 5-7.

Figure 5:
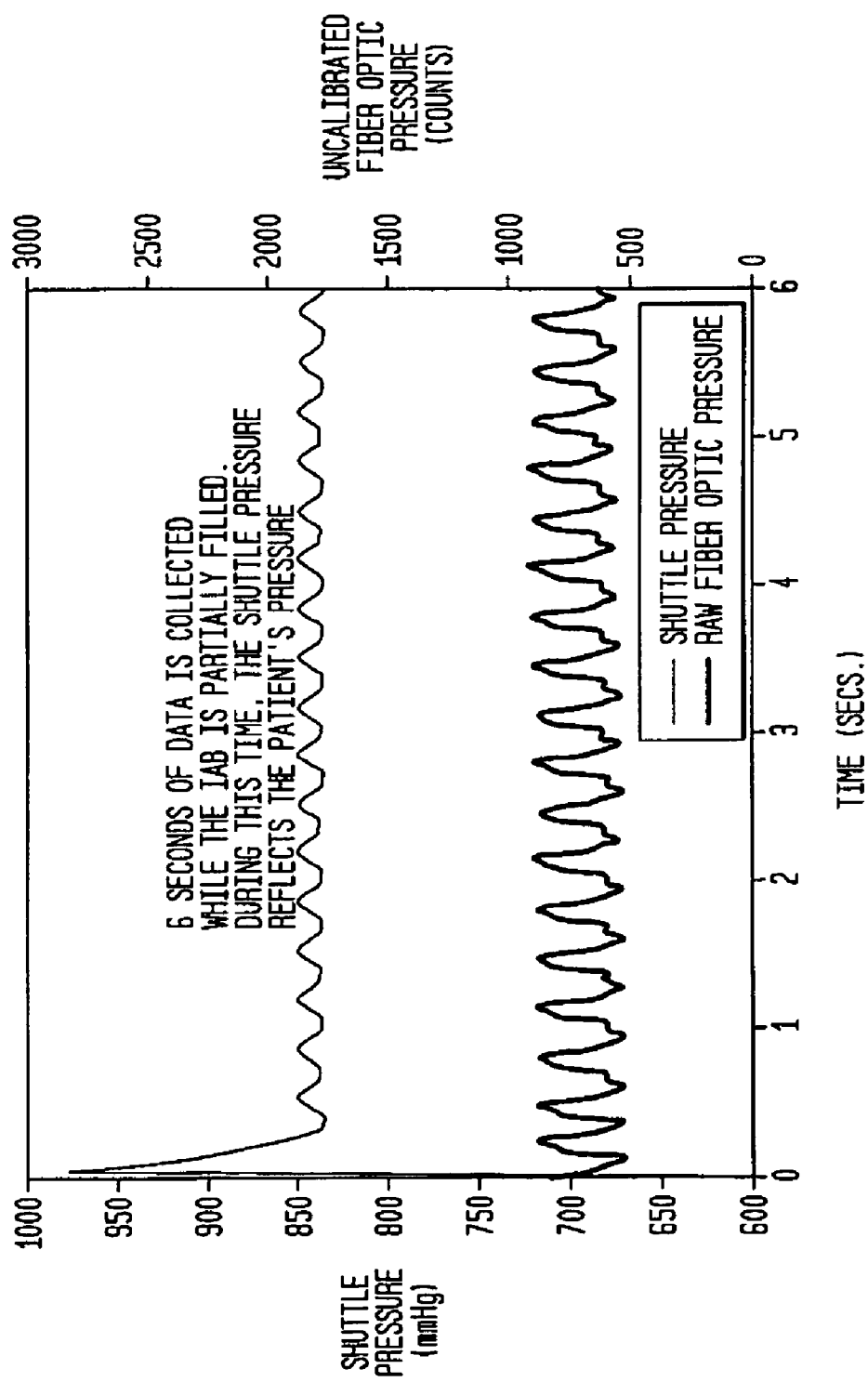
FIG. 5 is a graph showing blood pressure measurements obtained via an IAB system balloon and blood pressure measurements obtained via a fiber optic sensor associated with the balloon.

FIG. 5 is a graph showing two sets of blood pressure measurements obtained simultaneously, one set being obtained via an IAB system balloon, and the other set being obtained via a fiber optic sensor associated with the balloon. Preferably, the data is collected using periodic digital samples for both the blood pressure as measured through the balloon and the blood pressure as measured by the fiber optic sensor. The samples are collected at a uniform sampling rate, or "sampling frequency," that is equal to 1/(the period between samples). A sample rate of 250 Hz was used.

At time t=0 seconds, the membrane 20 is toggled to partially inflate the balloon. The partial inflate results in a momentary spike that can be observed on the shuttle pressure sensor. A fraction of a second after the membrane is toggled the shuttle pressure stabilizes. In an illustrative embodiment, all 6 seconds of data shown in FIG. 5, both balloon-based data and fiber optic sensor data, are collected for use in calibration.

Figure 6A:
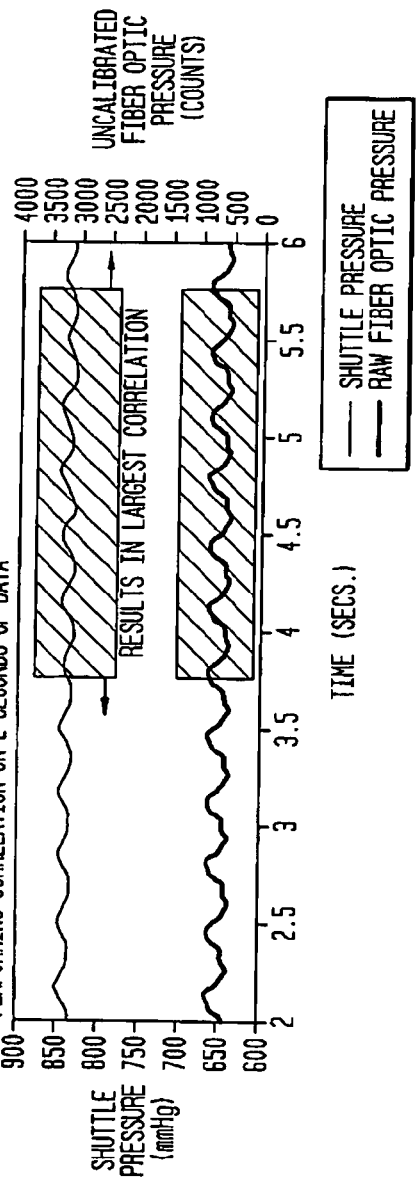
FIGS. 6A and 6B are graphs showing how a correlation process is used to determine the relative time delay between blood pressure measurements obtained from an IAB system balloon and blood pressure measurements obtained from a fiber optic sensor associated with the balloon.
Figure 6B:
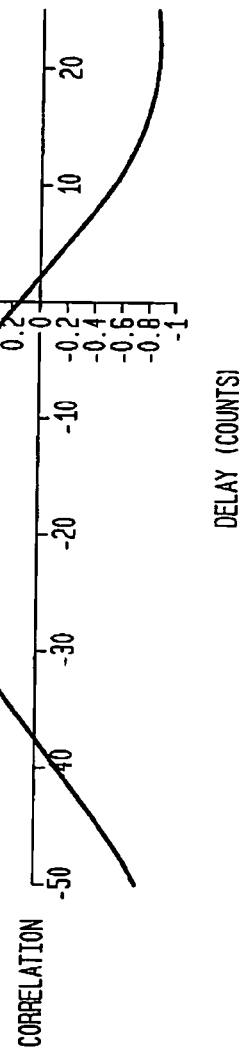

FIGS. 6A and 6B are graphs showing how a correlation process is used to determine the relative delay between the blood pressure measurements obtained through the IAB system balloon and the blood pressure measurements obtained from the fiber optic sensor. FIG. 6A shows seconds two through six of the data collected for both the blood pressure as measured through the balloon and the blood pressure as measured by the fiber optic sensor. Since the blood pressure incident on the balloon must propagate through the shuttle gas and associated shuttle gas apparatus before it is measured at the shuttle gas pressure sensor 25, the receipt of balloon-based data is filtered and delayed relative to the receipt of fiber optic data, which is transmitted optically and is received instantaneously in comparison to the data from the balloon. The relative delay between the balloon-based data and the fiber optic data is calculated and then used to time-align the balloon-based data and fiber optic data such that the two types of data can be properly compared.

In one embodiment, the relative delay between the balloon-based data and the fiber optic data is determined by performing a correlation between a two second window of the balloon-based data and the corresponding two second window of the fiber optic data. FIG. 6B shows the results of such a correlation performed on the FIG. 6A data. As can be seen from FIG. 6B, the best time alignment occurs at a point in time corresponding to the peak of the correlation function, i.e. when the data from the fiber optic sensor is delayed by 17 sampling periods (68 msecs) relative to the data received through the balloon. Accordingly, the correlation indicates that the shuttle gas system delays receipt of the balloon-based data by 17 sampling periods relative to receipt of the fiber optic data. Of course, the 17 sample delay was computed for a particular test system under particular conditions and the delays for various embodiments may vary, as may the delays computed for a particular embodiment under various conditions. Thus, the embodiments address the delay issue by estimating the relative time delay between the shuttle gas and fiber optic signal paths, and re-aligning the shuttle gas and fiber optic signals to compensate for the relative delay.

Once the appropriate shifting has been applied to the fiber optic calibration data, the fiber optic data can be compared to the balloon-based calibration data.

In an embodiment, the amplitude of seconds 2 through 6 of the balloon pressure data and the shifted fiber optic pressure data are independently sorted. This sorting process minimizes non-linear effects that may appear on the balloon pressure and ensures a matching of the "nth-largest" value of the balloon-based data to the "nth-largest" value of the fiber optic data where n ranges from 1 to the number of samples recorded for each type of data. That is, the balloon-based data and fiber optic data are rank-ordered from minimum to maximum.

Further, an exclusion process is performed on the sorted data. More specifically, after the two types of data have been sorted, an equal number of extreme values are dropped from the "top" and "bottom" of each ranked list. That is, only the "middle" portions of the ranked lists are considered.

Figure 7:
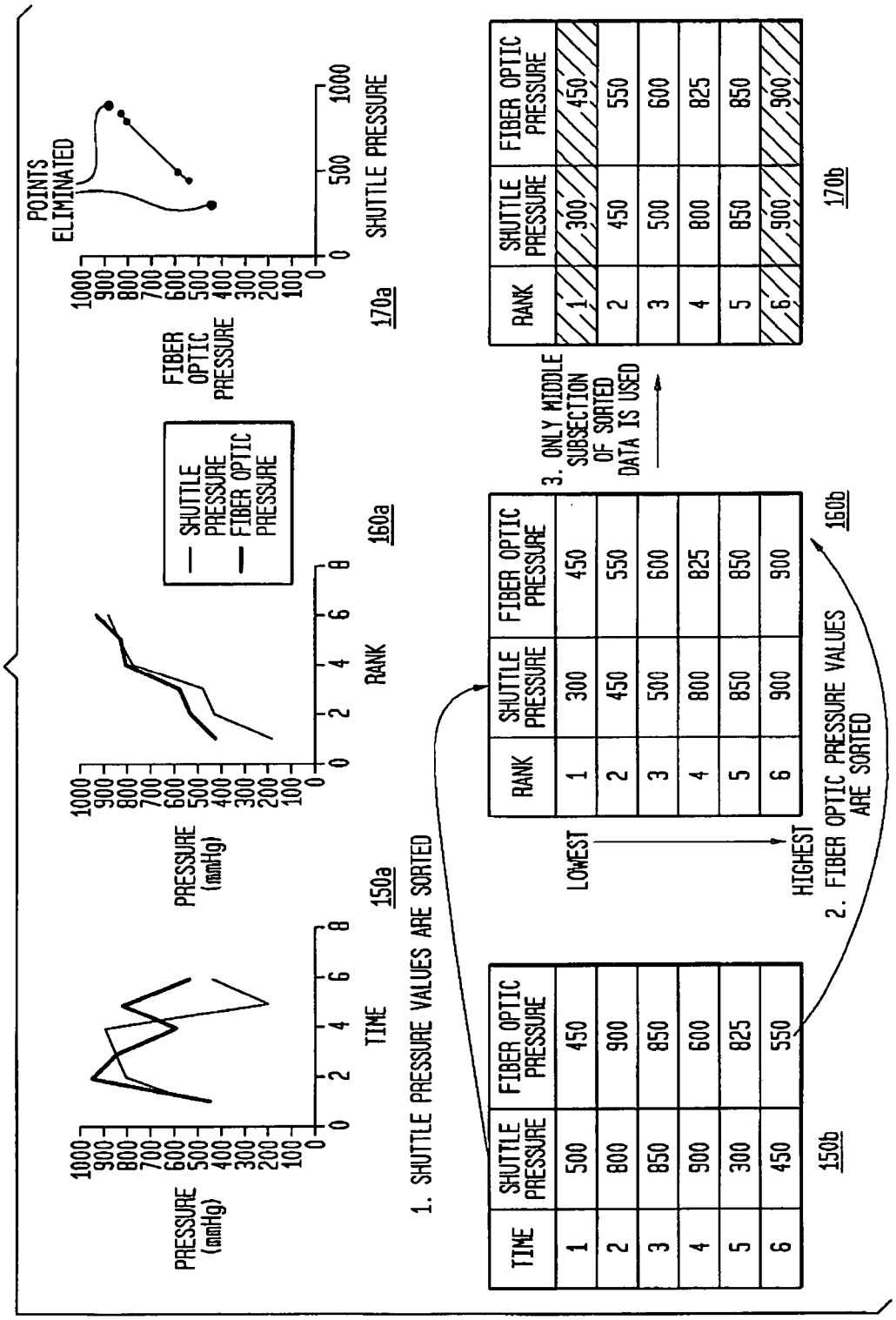
FIG. 7 provides a simplified example of data sorting and data exclusion processes in accordance with an embodiment.

FIG. 7 shows a simplified example of how the sorting and exclusion processes work. The data values considered in the example are not consistent with the data values considered in FIGS. 5, 6A, and 6B. In FIG. 7, six illustrative samples of balloon-based data and six illustrative samples of fiber optic data are plotted in a graph 150a of pressure vs. time. A table 150b lists the plotted samples in time order. In table 160b, the samples have been ranked from lowest value to highest value. Graph 160a is a pressure vs. rank graph depicting the ranked samples. The process by which the data of 150a and 150b is transformed into the data of 160a and 160b is the sorting process. The exclusion process is depicted in graph 170a and table 170b. Graph 170a is a graph of balloon-based data vs. fiber optic data, and it highlights the extreme points that are eliminated by the exclusion process. Table 170b is the same as table 160b, with the exception that the points eliminated by the exclusion process are highlighted.

The sorting and exclusion processes have two beneficial effects. First, extreme points ("outliers") are excluded from the calibration process. Second, data points from the peaks and valleys of the blood pressure waveform are excluded from the calibration process. In particular, the processes exclude data which is most likely to be corrupted by the poor fidelity (i.e. the "filtering effects") of the shuttle gas sensor.

It should be noted that the sorting and exclusion processes are optional features of the embodiments and the embodiments may be practiced without such features.

Once sorting and exclusion has been performed, the offset is calculated by averaging the differences between the resulting data pairs. In the example of FIG. 7, the offset of the fiber optic sensor is 56.25 mmHg, or $((550-450)+(600-500)+(825-800)-(850-850))/4$.

The negative of the computed offset may then be used as correction data to compensate for the sensor offset. Thus, for instance, the negative of the computed offset may be used as the offset component of the equation shown in FIG. 2A. Using the illustrative values of FIGS. 2A and 7, such substitution would result in a new equation of $y=1.0027x-56.25$. Accordingly, following calibration the equation $y=1.0027x-56.25$ is applied to a sensor reading of "x" to yield an approximation "y", the residual compensation for "x" is determined from the FIG. 2B data, and the residual compensation is applied to "y" to yield the calibrated blood pressure associated with the sensor reading of "x".

In the embodiment of FIG. 3, calibration of the IAB system of FIG. 1 involves temporarily suspending IAB assist, removing shuttle gas from the system, and collecting calibration data. After calibration data is collected, the shuttle gas is restored and assist is resumed. In an alternative to the FIG. 3 embodiment, the need to remove and restore shuttle gas is eliminated. This speeds the overall calibration process, and thereby permits quicker resumption of assist. Accordingly, such alternative embodiment is referred to as the "quick embodiment."

Figure 8:
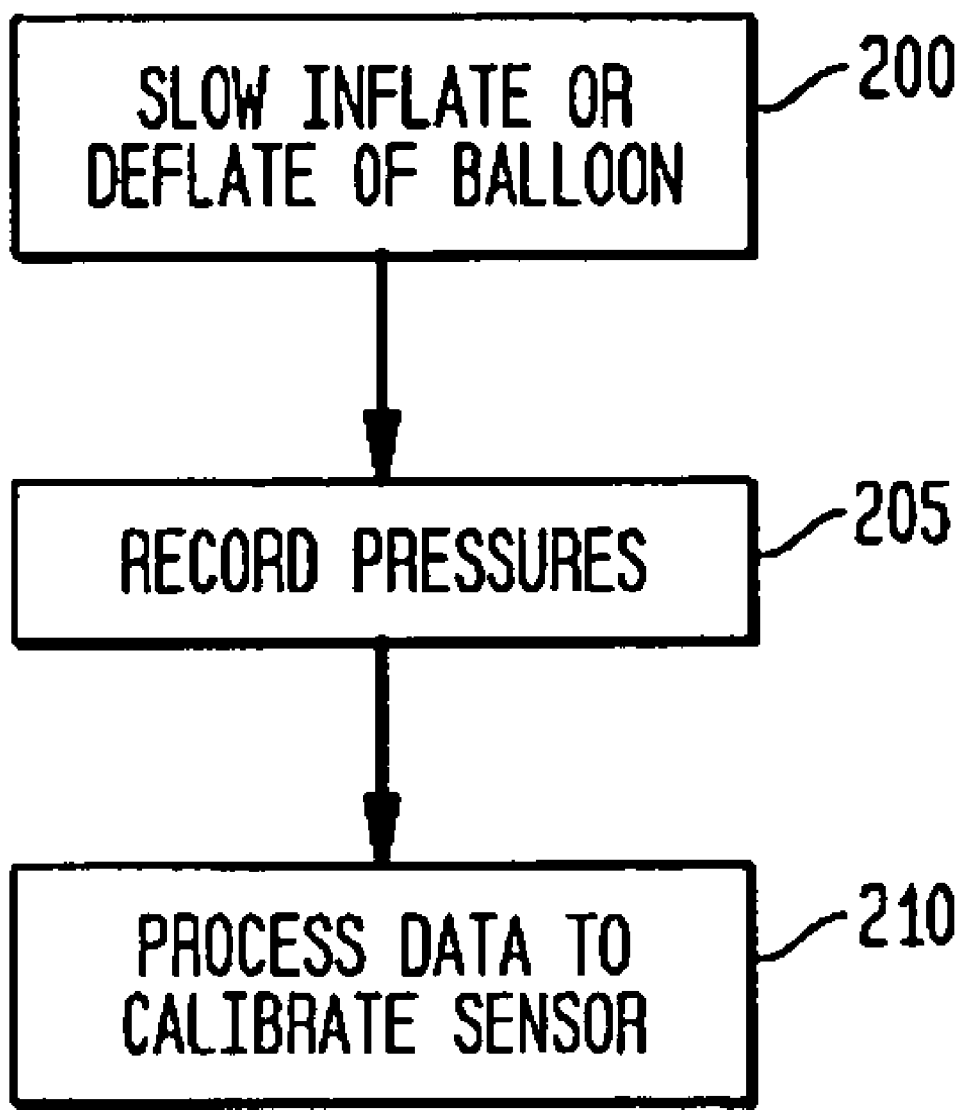
FIG. 8 is a flow chart showing how the IAB system of FIG. 1 is calibrated in accordance with an alternative embodiment.

FIG. 8 is a flow chart showing how the quick embodiment is implemented in the context of the IAB system of FIG. 1. As can be seen from FIG. 8, the first step in the quick embodiment involves a slow inflate or slow deflate of the balloon (step 200). As the balloon is slowly inflating or slowly deflating, balloon-based blood pressure measurements and fiber optic blood pressure measurements are simultaneously recorded for a period of time (step 205). The recorded measurements are then processed to calibrate the fiber optic sensor (step 210).

Preferably, the processing performed in step 210 accounts for the relative delay between the balloon-based measurements and the fiber optic measurements. In addition, it is preferred that the processing performed in step 210 accounts for the relative delay between the balloon based measurements and the fiber optic measurements in the same manner as discussed in connection with the FIG. 3 embodiment. Accordingly, for the remainder of the quick embodiment description, it should be understood that the relative delay is accounted for in the same manner as discussed in connection with the FIG. 3 embodiment. Nevertheless, for the sake of brevity of description there will be no further discussion of relative-delay processing in the quick embodiment.

In the quick embodiment, the degree of balloon under-inflation must fall within an acceptable range. That is, the shuttle pressure signal reflects patient blood pressure only when the degree of balloon under-inflation is within an acceptable range. If the balloon under-inflation is above or below the acceptable range, the shuttle gas pressure signal is completely or partially corrupted.

In one implementation of the quick embodiment, under-inflation of the balloon is achieved by slowing down the normal inflation process. Normally, during assist, complete inflation of the balloon is achieved within a fraction of a cardiac cycle (e.g. within about ⅛ of a second). For purposes of calibration, this process is slowed such that multiple cardiac cycles (e.g. 3 or 4 seconds) are required to achieve full inflation. During this slow inflation process, calibration data is collected on a continuous basis. The collected data is then processed to detect a time interval during which the shuttle gas pressure signal exhibits fidelity sufficient for performing calibration.

The slow inflation and/or slow deflation required in the quick embodiment can be achieved using the FIG. 1 configuration or by using a modified version of the FIG. 1 configuration. If the FIG. 1 configuration is used without modification, valves 30, 34, and/or 36 can be pulse-width modulated in order to achieve the desired flow rate to/from the primary side of isolator 18. In one possible modified configuration, valves 30 and 34 could be replaced by two valves each, such that the rate of flow through each of their respective pathways could be controlled by choosing between the opening of no valves, the opening of one valve, and the opening of two valves. For example, for a relatively slow rate of flow through the pathway corresponding to valve 30 a first valve associated with the pathway could be opened while a second valve associated with the pathway remains closed; whereas, for a relatively fast rate of flow both the first and second valves could be opened.

In one embodiment of such modified configuration, in each pair of valves that replaces valves 30 and 34, one of the valves has an orifice that is smaller than the orifice of the other valve so that the flow rate through the valve with the smaller orifice is throttled. As an alternative, one of the valves of each pair is placed in series with a restrictive orifice so as to throttle the flow rate through the valve.

It should be noted that the embodiments are not limited to employing pulse-width modulation and/or multiple valves for each source. Upon viewing this disclosure, one skilled in the art will readily appreciate the wide range of schemes that may be used to achieve the slow inflation and/or slow deflation of the quick embodiment. For example, a mechanically driven bellows can be used in lieu of some or all of the drive unit elements depicted in FIG. 1, with the rate of movement of the bellows being controlled to, in turn, control the rate of slow inflation and/or slow deflation. Moreover, it should be noted that a bellows can be used in the FIG. 3 embodiment, with static partial-inflation of the balloon being achieved by partially stroking the bellows.

Regarding static partial-inflation, it is further noted that as an alternative to the FIG. 3 and bellows implementations static partial-inflation can be achieved by using a valve in series with catheter 12. Such valve can be closed at a time that truncates balloon inflation to yield a desired target volume in the balloon. Similarly, the valve may be closed at a time that truncates balloon deflation to yield a desired target volume in the balloon.

In any case, since the fiber optic sensor has intrinsic high fidelity, it is used as a reference for determining the shuttle gas pressure signal's fidelity. In particular, the fidelity of the shuttle gas pressure signal is judged by correlating the shuttle gas pressure signal with the fiber optic sensor signal. Such correlation is performed in a manner similar to that described with respect to FIGS. 6A and 6B. Through use of the correlation results, a portion of the collected calibration data is selected for use in the calibration calculation (e.g. offset calculation). More specifically, a "selected time interval" in which the correlation exceeds a predetermined threshold is determined and the calibration data corresponding to the selected time interval is used in the calibration calculation.

In an embodiment, the mean value for each of the gas pressure signal and the fiber optic signal is subtracted from its respective signal prior to correlation so that the signals' DC components do not affect the correlation results. Thereby, assuring that the correlation is maximized when the pulsatile components of the signals are best matched.

In one embodiment, data capture continues until either the correlation peak lasts for at least 3 cardiac cycles or a data collection time limit is exceeded (e.g. 6 seconds is exceeded). When either of these events is detected, slow inflation is terminated and data collection is stopped. Normal IAB assist is resumed on the next cardiac cycle.

An offset for the fiber optic sensor is determined based on the calibration data collected during the selected time interval. It should be noted that in the quick embodiment, as in the embodiment of FIG. 3, the fiber optic measurements that are used to compute an offset may be "raw" fiber optic measurements. That is, they may be measurements obtained through the fiber optic sensor with no applied correction. Alternatively, the fiber optic measurements that are used to compute the offset may be corrected measurements, in which case the offset computed may be an offset that is relative to a previously stored offset. In any event, the data collected during the selected time interval may be used to compute the offset in the same manner as described in connection with the FIG. 3 embodiment.

Figure 9:
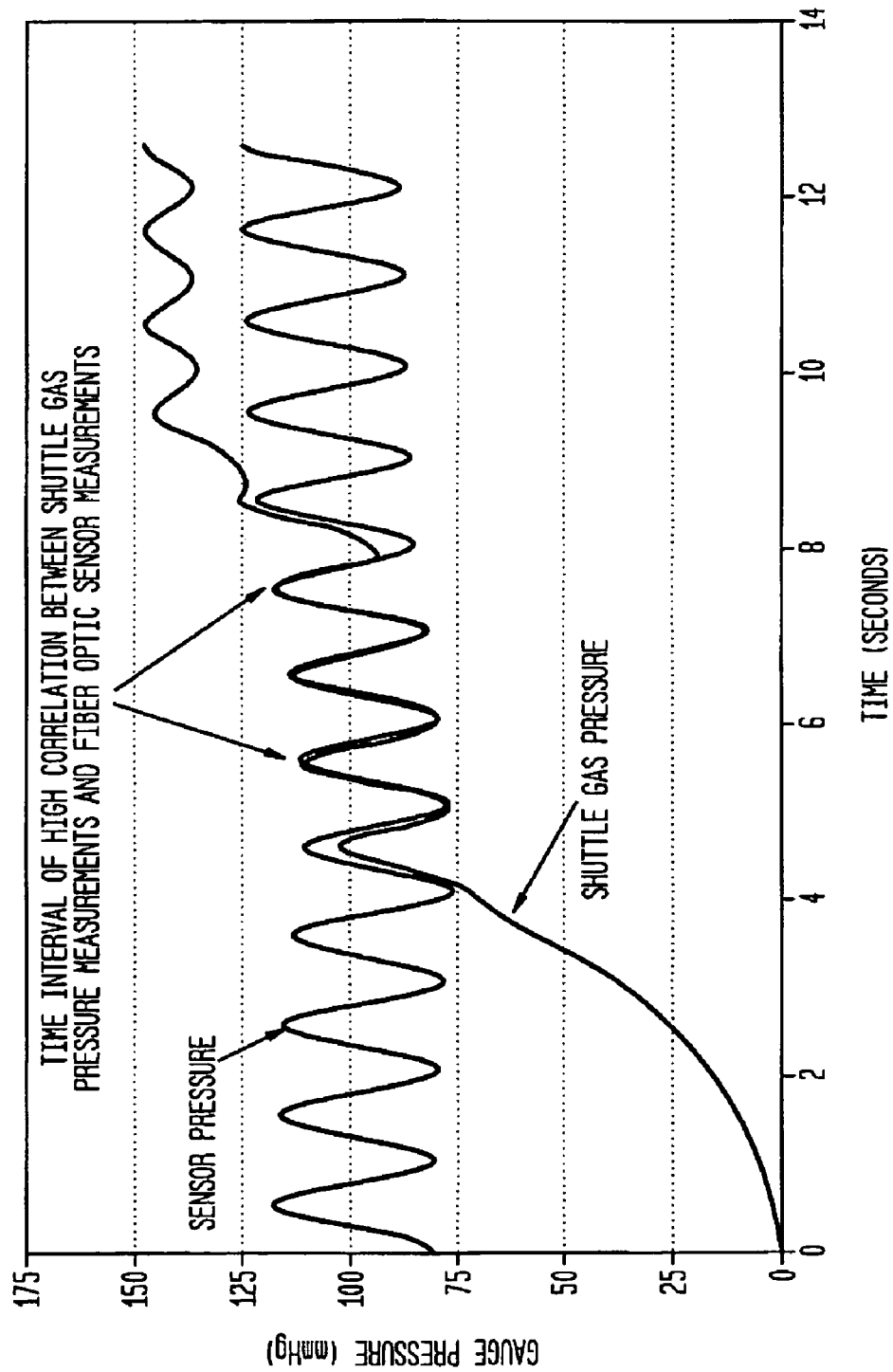
FIG. 9 is a graph illustrating the shuttle gas pressure and fiber optic sensor signals produced during a slow inflation process.

FIG. 9 is a graph illustrative of the shuttle gas pressure and fiber optic sensor signals produced during a slow inflation process. To generate the FIG. 9 data, a sinusoidal pressure waveform was simultaneously applied to both the shuttle gas pressure sensor and the fiber optic pressure sensor. The sensors were not used to monitor actual patient blood pressure. Further, for purposes of illustration, the shuttle gas pressure sensor and the fiber optic sensor were selected so as to minimize the differences between their sensitivities and offsets. Consequently, in FIG. 9 there is a high degree of similarity between the waveforms during the interval of optimum correlation.

Figure 10:
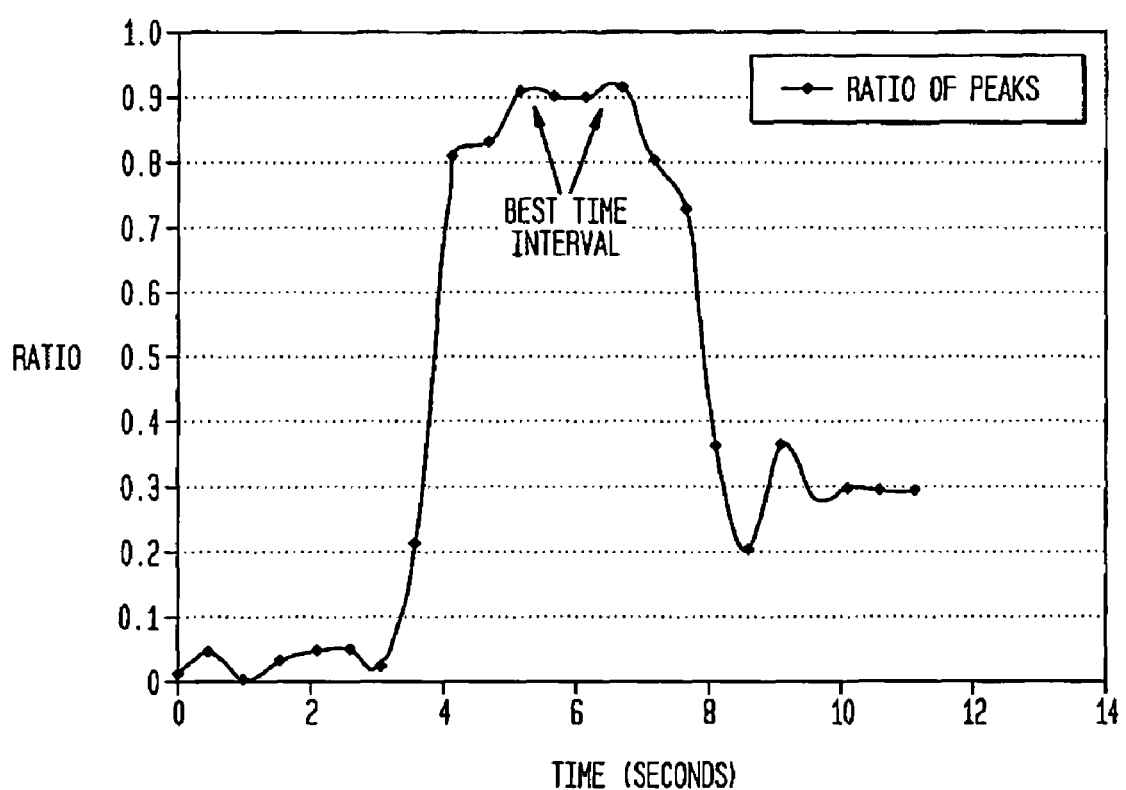
FIG. 10 is a plot of peak amplitude ratios based on the data depicted in FIG. 9.

As an alternative to performing correlation to determine a selected time interval, the following procedure may be invoked to determine a selected time interval: (1) compute the peak amplitudes of the pulses as measured by the gas pressure sensor; (2) compute the peak amplitudes of the pulses as measured by the fiber optic pressure sensor; (3) for each corresponding pair of peak amplitudes measured in (1) and (2), compute the ratios of peak pulse amplitudes (i.e. divide each peak amplitude as measured through the shuttle gas channel by the corresponding peak amplitude as measured through the fiber optic channel); and (4) set the selected time interval to a time interval in which the computed ratios exceed a predetermined threshold. FIG. 10 is a plot of peak pulse amplitude ratios based on the data depicted in FIG. 9. As can be seen from FIG. 10, if a predetermined threshold of 0.80 is used, the selected time interval is approximately 4 seconds to 7 seconds.

As another alternative, a selected time interval may be determined based solely on data from the shuttle gas pressure sensor. In such embodiment, the peaks and valleys of the pulses reflected in the shuttle gas pressure signal are detected and measured, and the resulting values are used to compute a "pulse height" for each pulse. The selected time interval is a time interval in which the computed pulse height exceeds a predetermined threshold.

Figure 11:
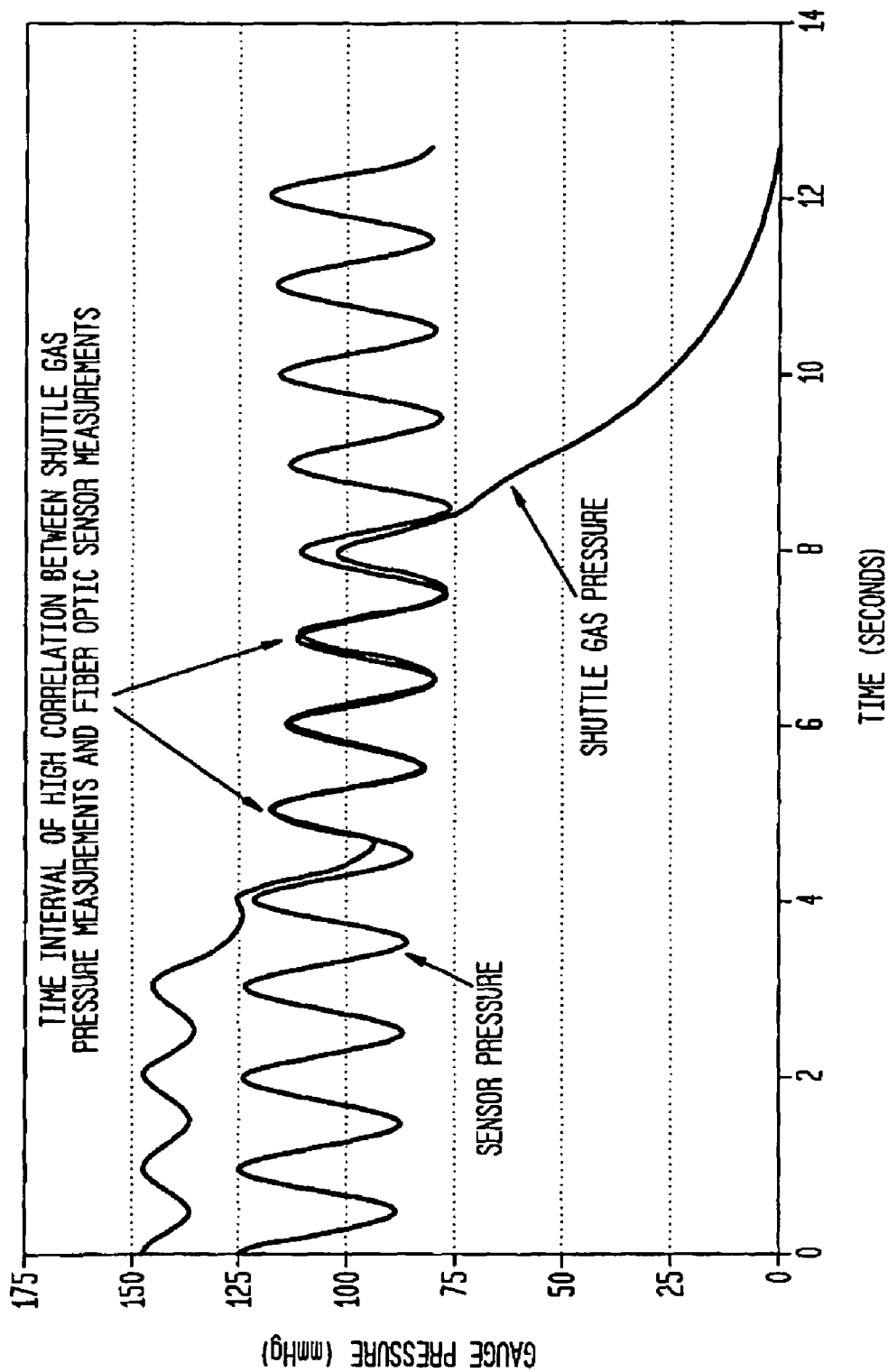
FIG. 11 is a graph illustrating the shuttle gas pressure and fiber optic sensor signals produced during a slow deflation process.

In an alternative to the embodiment in which the balloon is slowly inflated, calibration data is collected while the balloon is slowly deflated. FIG. 11 is a graph illustrative of the shuttle gas pressure signal and the fiber optic sensor signal produced during a slow deflation process. During such slow deflation process, calibration data is collected on a continuous basis. Calibration of the fiber optic sensor may then be carried out in any of the manners discussed in connection with the slow inflation embodiment.

Although the invention herein has been described with reference to particular embodiments, it is to be understood that these embodiments are merely illustrative of the principles and applications of the present invention. It is therefore to be understood that numerous modifications may be made to the illustrative embodiments. Still other embodiments may be devised without departing from the spirit and scope of the present invention as set forth in the following brief statements of certain preferred embodiments of the invention.

The invention claimed is:

1. An apparatus for performing an in-vivo calibration of a blood pressure sensor that is associated with a balloon of an in-vivo balloon system, comprising:
   a drive unit configured to control at least one of an inflation state and a deflation state of the balloon, the control comprising slowing a normal inflation and/or deflation process associated with cardiac assist such that the balloon transitions through a state in which a gas pressure in the balloon system is indicative of a patient's blood pressure without suspending the inflation or deflation of the balloon; and
   a processing unit configured to monitor the patient's blood pressure by observing the gas pressure in the balloon system while simultaneously monitoring the patient's blood pressure through the sensor, and configured to use the blood pressure readings obtained by monitoring the gas pressure to correct the blood pressure measurements obtained through the sensor.

2. The apparatus as recited in claim 1, wherein the sensor and the balloon are associated such that the sensor is in-vivo when the balloon is in-vivo.

3. The apparatus as recited in claim 1, wherein the blood pressure readings obtained by monitoring the gas pressure are used as reference blood pressure measurements and the processing unit is configured to generate correction data based on the relationship between the blood pressure measurements obtained through the sensor and the reference blood pressure measurements.

4. The apparatus as recited in claim 3, wherein the processing unit modifies further blood pressure measurements obtained through the sensor according to the correction data in combination with additional correction data so as to generate calibrated blood pressure measurements.

5. The apparatus as recited in claim 4, wherein the additional correction data comprises sensitivity correction data.

6. The apparatus as recited in claim 3, wherein the correction data comprises an offset correction.

7. The apparatus as recited in claim 1, wherein monitoring the patient's blood pressure comprises recording a pressure signal generated by a gas pressure sensor and a pressure signal generated by the blood pressure sensor.

8. The apparatus as recited in claim 7, wherein both the pressure signal generated by the gas pressure sensor and the pressure signal generated by the blood pressure sensor are made up of periodic samples.

9. The apparatus as recited in claim 1, wherein monitoring the patient's blood pressure comprises recording a pressure signal generated by a gas pressure sensor and a pressure signal generated by the blood pressure sensor, and using blood pressure readings comprises performing a time-alignment of the pressure signal generated by the gas pressure sensor and the pressure signal generated by the blood pressure sensor.

10. The apparatus as recited in claim 1, wherein using blood pressure readings comprises:
determining a selected time interval within which the gas pressure in the balloon system is substantially indicative of the patient's blood pressure.

11. The apparatus as recited in claim 10, wherein determining selected time interval comprises determining peak amplitudes of pulses of the gas pressure and the blood pressure, computing the ratio of the peak amplitudes of the pulses of the gas pressure and the blood pressure, and setting the selected time interval to a time interval in which the computed ratios exceed a predetermined threshold.

12. The apparatus as recited in claim 1, wherein the drive unit is configured to maintain the gas pressure in the balloon system during monitoring.

13. The apparatus as recited in claim 1, wherein the processing unit is configured to monitor the pressures without removing shuttle gas from the balloon system during calibration.

14. An intra-aortic balloon pump comprising:
a drive unit configured to communicate with an intra-aortic balloon catheter, the intra-aortic balloon catheter being connected to a balloon, the drive unit configured to control an inflation and deflation of the balloon, and the control comprising slowing a normal inflation and/or deflation process associated with cardiac assist, and
a processing unit configured to monitor a patient's blood pressure by monitoring the pressure within the balloon without suspending the inflation or deflation of the balloon.

15. The intra-aortic balloon pump of claim 14, wherein the intra-aortic balloon pump includes an associated blood pressure sensor, and
wherein the processing unit is configured to correct blood pressure measurements from the blood pressure sensor based on the patient's blood pressure as monitored by monitoring the pressure within the balloon.

16. The intra-aortic balloon pump as recited in claim 15, wherein the sensor and the balloon are associated such that the sensor is in-vivo when the balloon is in-vivo.

17. The intra-aortic balloon pump as recited in claim 15, wherein blood pressure readings obtained by monitoring the pressure within the balloon are used as reference blood pressure measurements and the processing unit is configured to generate correction data based on the relationship between blood pressure measurements obtained through the sensor and the reference blood pressure measurements.

18. The apparatus as recited in claim 14, wherein the drive unit is configured to control the pressure in the balloon to remain between an assist pressure of the inflation state and an assist pressure of the deflation state during monitoring.

19. The apparatus as recited in claim 14, wherein the processing unit is configured to monitor the pressures without removing shuttle gas from the balloon pump during calibration.

20. The apparatus as recited in claim 15, wherein monitoring the patient's blood pressure comprises recording a pressure signal generated by a gas pressure sensor and a pressure signal generated by the blood pressure sensor, and determining a selected time interval within which a gas pressure in the balloon system is substantially indicative of the patient's blood pressure, and
wherein determining the selected time interval comprises determining peak amplitudes of pulses of the gas pressure and the blood pressure, computing the ratio of the peak amplitudes of the pulses of the gas pressure and the blood pressure, and setting the selected time interval to a time interval in which the computed ratios exceed a predetermined threshold.

* * * * *